United States Patent
Celewicz et al.

(10) Patent No.: US 9,301,956 B2
(45) Date of Patent: Apr. 5, 2016

(54) APPLICATION OF CINCHONA ALKALOID DERIVATIVES AS CYTOTOXIC COMPOUNDS

(71) Applicant: ADAM MICKIEWICZ UNIVERSITY, Poznań (PL)

(72) Inventors: Lech Celewicz, Poznań (PL); Karol Kacprzak, Pecna (PL); Piotr Ruszkowski, Suchy Las (PL)

(73) Assignee: ADAM MICKIEWICZ UNIVERSITY, Poznań (PL)

( * ) Notice: Subject to any disclaimer, the term of this patent is extended or adjusted under 35 U.S.C. 154(b) by 0 days.

(21) Appl. No.: 14/430,168

(22) PCT Filed: Mar. 4, 2014

(86) PCT No.: PCT/PL2014/050011
§ 371 (c)(1),
(2) Date: Mar. 20, 2015

(87) PCT Pub. No.: WO2015/041551
PCT Pub. Date: Mar. 26, 2015

(65) Prior Publication Data
US 2016/0022668 A1    Jan. 28, 2016

(30) Foreign Application Priority Data
Feb. 12, 2014   (PL) .......................................... 407154

(51) Int. Cl.
*A61K 31/49*   (2006.01)
(52) U.S. Cl.
CPC ..................................... *A61K 31/49* (2013.01)
(58) Field of Classification Search
CPC ..................................................... A61K 31/49
USPC ....................................................... 514/305
See application file for complete search history.

(56) References Cited

U.S. PATENT DOCUMENTS

| | | | | |
|---|---|---|---|---|
| 5,635,515 A * | 6/1997 | Chauffert | ............... | A61K 31/49 514/305 |
| 6,528,524 B2 * | 3/2003 | Genne | .................... | A61K 31/49 514/305 |
| 7,557,142 B2 * | 7/2009 | Campbell | .............. | A61K 31/10 514/562 |

FOREIGN PATENT DOCUMENTS

| | | |
|---|---|---|
| EP | 1 477 488 A1 | 11/2004 |
| PL | 215 451 B1 | 12/2013 |

OTHER PUBLICATIONS

Hladon et al.; "In Vitro Cytostatic Activity of 8-Substituted and Tricyclic Analogues of Acyclovir;" Polish Journal of Pharmacology; 2002; pp. 45-53; vol. 54.
Vichai et al.; "Sulforhodamine B colorimetric assay for cytotoxicity screening;" Nature Protocols; 2006; pp. 1112-1116; vol. 1, No. 3.
Fattorusso et al.; "Antitumor Alkaloids in Clinical Use or in Clinical Trials;" Modern Alkaloids: Structure, Isolation, Synthesis and Biology; 2008; pp. 25-52.
Solary et al.; "Phase I study of cinchonine, a multidrug resistance reversing agent, combined with the CHVP regimen in relapsed and refractory lymphoproliferative syndromes;" Leukemia; 2000; pp. 2085-2094; vol. 14.
Martirosyan et al.; "Differentiation-inducing quinolines as experimental breast cancer agents in the MCF-7 human breast cancer cell model;" Biochemical Pharmacology; 2004; pp. 1729-1738; vol. 68.
Lee et al.; "Hydrocinchonine, Cinchonine, and Quinidine Potentiate Paclitaxel-Induced Cytotoxicity and Apoptosis via Multidrug Resistance Reversal in MES-SA/DX5 Uterine Sarcoma Cells;" Environmental Toxicology; 2011; pp. 424-431; vol. 26.
Oct. 13, 2014 International Search Report from International Application No. PCT/PL2014/050011.
Oct. 13, 2014 Written Opinion of the International Searching Authority from International Application No. PCT/PL2014/050011.

* cited by examiner

*Primary Examiner* — My-Chau T Tran
(74) *Attorney, Agent, or Firm* — Oliff PLC

(57) ABSTRACT

9-O-propargyl ethers of cinchona alkaloids of general formula represented by formula 1

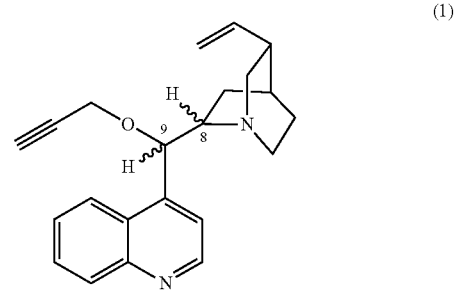

wherein respective ethers have the following absolute configuration at C-8 and C-9 atoms:
  (8R,9S)-cinchonine configuration or
  (8R,9R)-9-epicinchonine configuration
are useful in treatments of at least one of breast cancer, cervical cancer, lung cancer and nasopharynx cancer.

5 Claims, No Drawings

APPLICATION OF CINCHONA ALKALOID DERIVATIVES AS CYTOTOXIC COMPOUNDS

The subject matter of the invention is the application of 9-O-propargylcinchonine for the manufacture of drugs used in anticancer treatment.

Cancer diseases are one of the principal health disorders reported in humans, having the highest mortality rates and increasing numbers of new cases, related first of all to the increased life length and to lifestyle. The treatment of cancer diseases is difficult, expensive and in many cases not efficacious. Therefore, there is an urgent need for novel substances with cytostatic activity. They are frequently sourced from natural products, in particular from alkaloids and derivatives thereof, such as taxol, camptothecin or *Vinca* alkaloids (for review, see Taglialatela-Scafati, O. *Modern Alkaloids*, Fattorusso E. (ed.), Wiley-VCH, 2007, p. 25). Cinchona bark alkaloids, such as for example quinine, quinidine and cinchonidine and cinchonine, do not have specific anti-cancer properties. In experimental therapies for cancer diseases with multi drug resistance (MDR), combinations of anti-cancer drugs have been used, such as cyclophosphamide, doxorubicin, methylprednisolone or vinblastine with not anticancer Cinchona alkaloids (quinine or cinchonine). These alkaloids inhibit the removal of the aforementioned anti-cancer drugs from multi-drug resistant cancerous cells, resulting in increase of the action of such drugs (Lee, S.-Y. et al. Environ. Tox., 2011, 26, 424 and Solary, E. et al., Leukemia, 2000, 14, 2085).

In the experimental anti-cancer differentiation therapy, in turn, compounds are used which may have an effect on the expression of genes associated with cancer growth combined with traditional chemotherapeutic agents which destroy cancerous cells. Weak inhibition of growth and differentiation of in vitro breast cancer cells (MCF-7) was reported for high concentrations of quinine and quinidine ($IC_{50}$: 40 and 113 µM, respectively) which according to chemotherapy standards not qualify these substances as active drugs (Martirosyan, A. R. et al. *Biochem. Pharmacol.*, 2004, 68, 1729).

The objective of the invention has been to develop novel applications of Cinchona alkaloid derivatives with cytotoxic activity in anti-cancer treatment.

The subject matter of the invention is the application of 9-O-propargyl ethers of a general formula represented by formula 1

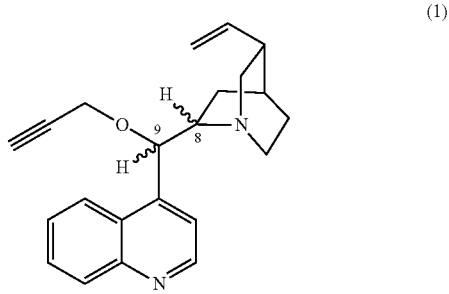

(1)

wherein respective ethers have the following absolute configuration at C-8 and C-9 atoms:
 (8R,9S)-cinchonine configuration or
 -(8R,9R)-9-epicinchonine configuration
for the manufacture of drugs used in cancer chemotherapy. Common numbering used in cinchona alkaloid chemistry was used to define the absolute configuration.

Cytotoxic activity tests were performed using the following cancer cell lines: MCF-7 (breast cancer), HeLa (cervical cancer) A549 (pulmonary cancer) and KB (nasopharynx cancer) obtained from ECACC (European Collection of Cell Cultures).

Cytotoxicity tests were carried out using a standard procedure with sulphorhodamine B. They involved incubation of the cancer cell lines in the logarithmic growth phase for 72 hours with the compound tested and, subsequently, spectrophotometric determination of the degree of cell growth inhibition using adsorption of a dye (sulphorhodamine B) which binds cellular proteins. The determination was carried out according to a procedure reported in: Vichai, V., Kirtikara, K. *Nature Protocols*, 2006, 1, 1112.

Preparation of Cells for the Experiment:

Cancerous cells of the cell line tested in the logarithmic growth phase were seeded onto 24-well plates in a quantity of 20,000 cells/2 mL of the growth medium per well and, subsequently, incubated in an incubator at 37° C., in the 5% CO2 atmosphere for 24 hours.

Preparation of Test Compound Solutions:

Solutions of the test compounds were prepared in DMSO in the following concentration range: 0.05; 0.1; 0.5; 1; 5; 10; 50; 100 µM.

The cells of the lines tested were treated with the solutions of the test compounds in a laminar-flow chamber which ensured sterile working conditions according to the following procedure: the first three wells were used as a control: they contained 20 µL of DMSO only; successive solutions of the test compound were added to subsequent wells (20 µL), starting with the lowest concentration (three wells for each concentration level). Subsequently, the plates were placed in an incubator for 72 hours.

After the end of incubation, the adhered cells were fixed by adding 500 µL of cold (4° C.) 50% trichloroacetic acid (TCA) and incubated at 4° C. for 1 hour. Subsequently, each well was rinsed with sterile water and dried. The operation was repeated five times. The fixed cells were stained for 30 minutes by adding 500 µL of 0.4% of a dye solution (sulphorhodamine B) dissolved in 1% acetic acid. Any unbound dye was removed by decanting it from the plate, and the cells were washed 4 times with 1% acetic acid. Subsequently, the plates were dried in air for approx. 5 minutes. Any unbound dye was dissolved by adding 1500 µL of 10 mM mM Tris-base buffer (trishydroxymethylaminomethane) to each well and shaken using an orbital shaker for 5 minutes. Subsequently, 200 µL of solution from each well was transferred to each of two wells on a new 96-well plate and absorption of the solutions was determined spectrophotometrically at a wavelength of 490-530 nm using a plate reader. Percentage inhibition of cell growth by the test compound was calculated assuming the absorption of the control solution as 100%.

Depending on the type of the cell line, the following growth media were used:
 the MCF-7 line was grown in Dulbecco's Modified Eagle's Medium (DME) from Sigma (cat. no. D5796),
 the HeLa, A549 and KB lines were grown in RPMI-1640 Medium from Sigma (cat. no. R8758).

$IC_{50}$ values, denoting concentration of a compound needed to obtain 50% inhibition of cell growth, were determined for all the derivatives tested. Derivatives for which $IC_{50}$<4 µg/mL are generally assumed as active (abbreviated as A), derivatives with values in an $IC_{50}$ range of 4-30 µg/mL are considered medium active (abbreviated as MA), while those for which $IC_{50}$>30 µg/mL are considered non-active (abbreviated as NA).

To enable comparison, identical tests were performed using known cytotoxic agents: 5-fluoro-2'-deoxyuridine and 5-fluorouracil as well as other cinchona alkaloids: cinchonine.

The results of cytotoxic activity tests for the compounds of general formula 1 are shown in Table 1. The values are average results of three independent determinations.

TABLE 1

| | Cytotoxic activity, $IC_{50}$ | | | | | | | |
|---|---|---|---|---|---|---|---|---|
| | MCF-7 line (breast cancer) | | HeLa (cervical cancer) | | A549 (lung cancer) | | KB (nasopharynx cancer) | |
| Compound | [µg/mL] | [µmol] | [µg/mL] | [µmol] | [µg/mL] | [µmol] | [µg/mL] | [µmol] |
| 9-O-propargylcinchonine (PCN) | 3.0 (A) | 9.02 | 3.5 (A) | 10.53 | 3.9 (A) | 11.73 | 3.2 (A) | 9.63 |
| cinchonine | >50 (MA) | — | >50 (MA) | — | >50 (MA) | — | >50 (MA) | — |
| 5-fluoro-2'-deoxyuridine | 2.81 | 11.4 (MA) | 3.20 | 13.0. (MA) | 3.30 | 13.4 (MA) | 3.37 | 13.7 (MA) |
| 5-fluorouracil | 2.37 | 18.2 (MA) | 2.73 | 21.0 (MA) | 2.78 | 21.4 (MA) | 2.86 | 22.0 (MA) |

The in vitro cytotoxicity against cancer cell lines of breast cancer, cervical cancer, lung cancer and nasopharynx cancer of the PCN compound is within the range of high activity. The cytotoxicity of compound PCN in each case was higher than that of currently used anti-cancer agents, such as 5-fluoro-2'-deoxyuridine and 5-fluorouracil.

The subject matter of the invention is the application of 9-O-propargylcinchonine (PCN) for the manufacture of drugs used in breast cancer chemotherapy.

The tests performed confirmed that PCN has the highest activity against the MCF-7 line with an $IC_{50}$ value of 3.0 µg/mL. It is more than two times as cytotoxic as 5FU, the control compound currently used in anti-cancer treatment, and 1.3 times as active as 5 FdU.

Another aspect of the invention is the application of 9-O-propargylcinchonine (PCN) for the manufacture of drugs used in cervical cancer chemotherapy.

The tests performed confirmed that PCN has the highest activity with an $IC_{50}$ value of 3.5 µg/mL. PCN is two times as cytotoxic as 5FU (the control compound) and 1.2 times as cytotoxic as 5 FdU.

Another aspect of the invention is the application of 9-O-propargylcinchonine (PCN) for the manufacture of drugs used in pulmonary cancer chemotherapy.

The tests performed confirmed that PCN has the highest activity with an $IC_{50}$ value of 3.9 µg/mL. PCN is more than 1.8 times as cytotoxic as 5FU (the control compound) and slightly more cytotoxic as 5 FdU.

Another aspect of the invention is the application of 9-O-propargylcinchonine (PCN) for the manufacture of drugs used in nasopharynx cancer chemotherapy.

The tests performed confirmed that PCN has the highest activity with an $IC_{50}$ value of 3.2 µg/mL. Compared to 5FU and 5 FdU, PCN has 2.3 and 1.4 times as high activity, respectively.

The cytotoxicity of compounds of general formula 1 is associated with absolute configuration at C-8 and C-9 atoms; the PCN compound with the highest activity is cinchonine derivative with (8R,9S) configuration, and a change to the opposite configuration, (8S,9R), found in the PCD derivative and cinchonidine from which it is prepared, leads to an about 3-fold reduction in cytotoxic activity.

The subject matter of the invention is explained by an embodiment which illustrates the synthesis of the PCN compound.

The Cinchona alkaloid 9-O-propargyl ether was prepared from a natural alkaloid isolated from Cinchona bark using a procedure disclosed in patent EP1477488.

EXAMPLE 1

Cinchonine (883 mg; 3 mmol) was dissolved in anhydrous DMF (12 mL); subsequently, the solution was placed on an ice bath. The mixture was cooled to approx. 5° C. and sodium hydride (50% NaH in mineral oil, 300 mg, 2 equivalents) was added portionwise over 0.5 hour. The solution was stirred for 2 hours and propargyl bromide as a 80% solution in toluene (0.42 mL; 3.75 mmol, 1.25 equivalents) was added using a syringe. The reaction mixture was left to stand overnight at room temperature. Subsequently, dichloromethane (50 ml) was added to the reaction mixture and the organic solution was washed sequentially with saturated NaCl solution (30 ml) and distilled water (30 mL). The organic layer was dried with anhydrous magnesium sulphate; subsequently, the drying agent was filtered off and the solvents were evaporated using a vacuum evaporator, maintaining the water bath temperature in the 40-45° C. range. The crude product, 9-O-propargylcinchonine (PCN), was purified on a chromatographic column with silica gel (60H, 0.045-0.075 mm/200-300 mesh from Merck) in the gradient: $CH_2Cl_2$/n-hexane, $CH_2Cl_2$, 1% $MeOH/CH_2Cl_2$, 5% $MeOH/CH_2Cl_2$. The PCN compound was obtained as oil with a purity of >99% and in yield of approx. 80%.

$^1$H NMR (300/400 MHz, $CDCl_3$): δ 1.24 (m, 1H), 1.52 (m, 2H), 2.11 (m, 1H), 2.28 (q, 1H, J=8.0 Hz), 2.46 (t, 1H, J=2.3 Hz), 2.72-2.97 (m, 3H), 3.11 (m, 1H), 3.49 (s, 1H), 3.92 (d, 1H, J=1.8 Hz), 3.95 (d, 1H, J=1.8 Hz), 4.21 (d, 1H, J=2.4 Hz), 4.25 (d, 1H, J=2.4 Hz), 5.01 (d, 1H, J=3.7 Hz), 5.14 (d, 1H, J=11.1 Hz), 6.10 (ddd, 1H, J=17.3, 10.1, 7.6 Hz), 7.26 (s, 1H), 7.48 (d, 1H, J=4.3 Hz), 7.59 (m, 1H), 7.73 (m, 1H), 8.15 (d, 1H, J=8.4 Hz), 8.18 (d, 1H, J=8.5 Hz), 8.91 (d, 1H, J=4.3 Hz)

$^{13}$C NMR ($CDCl_3$): δ 20.35, 28.10, 40.00, 49.22, 49.98, 56.48, 60.30, 75.13, 114.74, 123.24, 126.81, 129.18, 130.46, 148.51, 150.08.

MS ES (m/z): (−) 331 (M−H)$^-$, 367/369 (M+Cl)$^-$; (+) 333 (M+H)$^+$, 355 (M+Na)$^+$.

The invention claimed is:
1. A method for treating at least one cancer selected from the group consisting of breast cancer, cervical cancer, lung cancer and nasopharynx cancer, comprising administering to a patient inflicted with the at least one cancer a drug compris- ing one or more 9-O-propargyl ethers of cinchona alkaloids of general formula represented by formula 1

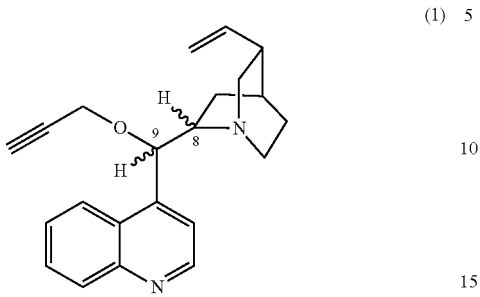

(1)

wherein respective ethers have the following absolute configuration at C-8 and C-9 atoms:
(8R,9S)-cinchonine configuration or
(8R,9R)-9-epicinchonine configuration.

2. The method of claim 1, wherein the at least one cancer is breast cancer.

3. The method of claim 1, wherein the at least one cancer is cervical cancer.

4. The method of claim 1, wherein the at least one cancer is pulmonary cancer.

5. The method of claim 1, wherein the at least one cancer is nasopharynx cancer.

* * * * *